US00PP22516P3

(12) United States Plant Patent

Kawashima et al.

(10) Patent No.: US PP22,516 P3

(45) Date of Patent: Feb. 21, 2012

(54) **NEW GUINEA *IMPATIENS* PLANT NAMED 'SAKIMP021'**

(50) Latin Name: *Impatiens×hybrida (I. hawkeri)*
Varietal Denomination: SAKIMP021

(75) Inventors: Moriya Kawashima, Amstelveen (NL); Michiyoshi Fuyama, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/802,707

(22) Filed: Jun. 11, 2010

(65) Prior Publication Data

US 2011/0307984 P1 Dec. 15, 2011

(51) Int. Cl.
*A01H 5/00* (2006.01)

(52) U.S. Cl. ..... Plt./318.4

(58) Field of Classification Search ..... Plt./318.1, Plt./318.4

See application file for complete search history.

(56) References Cited

OTHER PUBLICATIONS

UPOV-ROM GTITM, Plant Variety Database, 2011,/01, GTI Jouve Retrieval Software, Citation for plant 'SAKIMP021'. (1 page).*

"The New Royal Horticultural Society Dictionary of Gardening", 1992, Macmillan Press Limited; vol. 2, pp. 649-651 (5 pages total).*

* cited by examiner

*Primary Examiner* — Susan McCormick Ewoldt

(74) *Attorney, Agent, or Firm* — Jondle & Associates, P.C.

(57) ABSTRACT

A New Guinea *Impatiens* plant particularly distinguished by having pink flowers, a strong root system, and vigorous plant growth habit, is disclosed.

1 Drawing Sheet

Genus and species: *Impatiens×hybrida* (*I. hawkeri*).
Variety denomination: 'SAKIMP021'.

BACKGROUND OF THE NEW PLANT

The present invention relates to a new and distinct variety of New Guinea *Impatiens*, botanically known as *Impatiens× hybrida* (*I. hawkeri*), and referred to by the variety name 'SAKIMP021'. 'SAKIMP021' originated from a hybridization between the female New Guinea *Impatiens* plant 'NG-02SM-1 3' (unpatented) and the male New Guinea *Impatiens* plant 'EL-1A-1' (unpatented) in Misato, Japan. The female parent plant resulted from a cross between *I. platypetala* and an *I. hawkeri*. The male parent is of an unknown wild species.

In June 2005, the female parent plant 'NG-02SM-1 3' and the male parent plant 'EL-1A-l' were crossed and a population of $F_1$ plants was created. The $F_1$ plants were evaluated in Misato, Japan in an open field trial. The criteria for plant selection included a pink flower color, strong root system, and a vigorous plant growth habit. At the completion of the trial, one single-plant selection was made based on the above criteria and vegetatively propagated. From May 2006 to August 2006, the selection was evaluated in an open field in Misato, Japan. Shoot-tip cuttings of the variety were then shipped to Salinas, Calif., where the plants were regenerated and reevaluated for stability of traits. The selection subsequently was named 'SAKIMP021' and found to have its unique characteristics reproduced true to type in successive generations of asexual propagation.

SUMMARY OF THE INVENTION

The following are the most outstanding and distinguishing characteristics of this new variety when grown under normal horticultural practices in Salinas, Calif.

1. Pink flower color;
2. Strong root system; and
3. Vigorous plant growth habit.

DESCRIPTION OF THE PHOTOGRAPHS

This new variety is illustrated by the accompanying photographs which show the overall plant habit including blooms, buds, and foliage of the plant. The colors shown are as true as can be reasonably obtained by conventional photographic procedures. The photographs are of plants that are five months from propagation by terminal cutting in Salinas, Calif., under greenhouse conditions.

DETAILED DESCRIPTION OF THE NEW VARIETY

Figure 1:
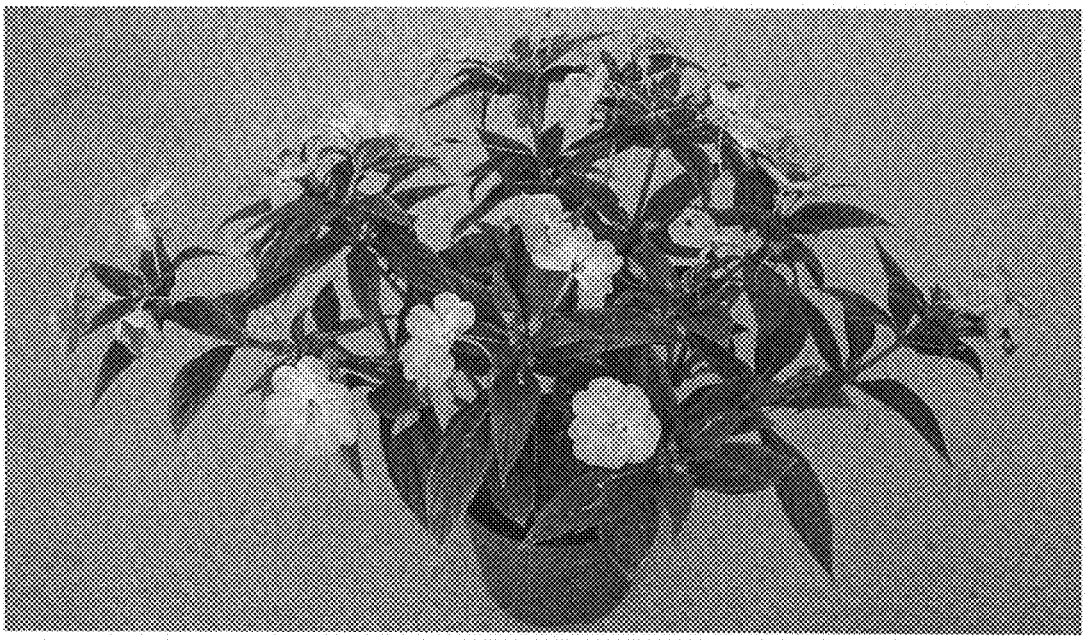
FIG. 1 shows overall plant habit including blooms, buds, and foliage.
Figure 2:
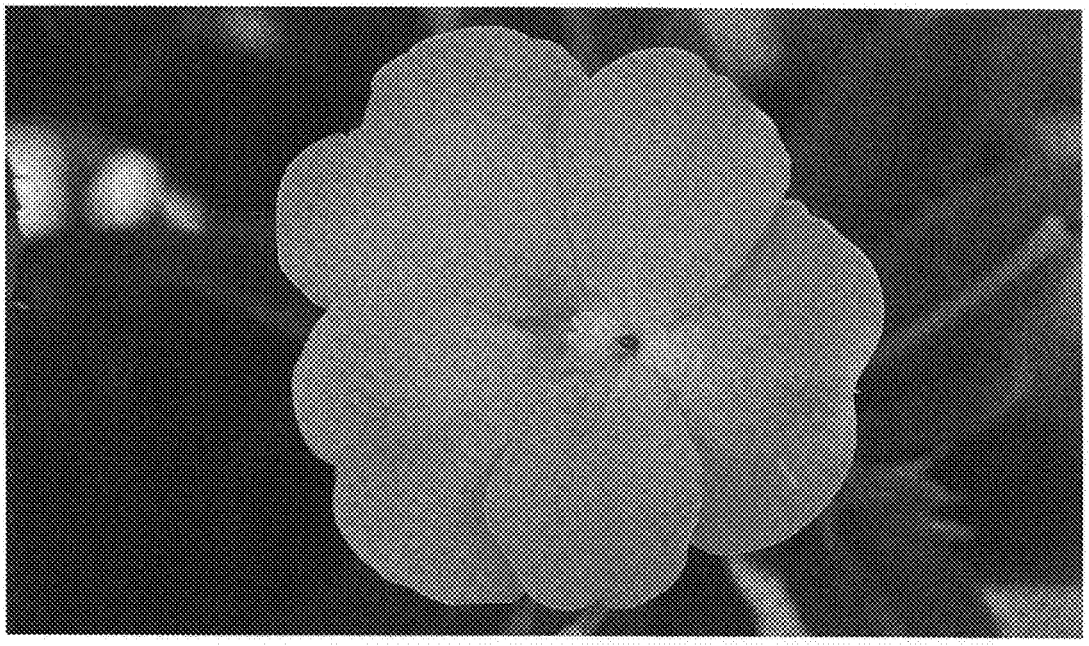
FIG. 2 shows the mature inflorescence.

The following detailed descriptions set forth the distinctive characteristics of 'SAKIMP021'. The data which define these characteristics were collected from asexual reproductions carried out in Salinas, Calif. The plant history was taken on plants grown for about five months from propagation by terminal cuttings under greenhouse conditions. Color references are primarily to The R.H.S. Colour Chart of The Royal Horticultural Society of London (R.H.S)., $4^{th}$ Edition (2001). Anatomic labels are from *The Cambridge Illustrated Glossary of Botanical Terms*, by M. Hickey and C. King, Cambridge University Press.

DETAILED BOTANICAL DESCRIPTION

Classification:

*Family.*—Balsaminaceae.

*Botanical.*—*Impatiens×hybrida* (*I. hawkeri*).

*Denomination.*—'SAKIMP021'.

*Common name.*—New Guinea *Impatiens*.

Parentage:

*Female parent.*—The proprietary New Guinea *Impatiens* plant 'NG-02SM-1 3' (unpatented).

*Male parent.*—The proprietary New Guinea *Impatiens* plant 'EL-1A-1' (unpatented).

Growth:

*Time to produce a rooted cutting.*—The terminal 1.0 inches to 1.5 inches of an actively growing stem was excised. The vegetative cuttings were propagated in five to six weeks. The base of each cutting was dipped for one to two seconds in a 1:9 solution of Dip 'N Grow (1 solution: 9 water) root inducing solution immediately prior to sticking into the cell trays. Cuttings were stuck into plastic cell trays having ninety-eight cells, and containing a moistened peat moss-based growing medium. The cuttings were misted with water from overhead for ten seconds every thirty minutes until sufficient roots were formed.

*Environmental conditions for plant growth.*—Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus, and 20% potassium was applied once a day or every other day by overhead irrigation. Plants were fertilized every two to three days, two times in consecutive applications and then given one clear water application. Pots were top-dressed with a dry, slow release fertilizer containing 14% nitrogen, 14% phosphorus, and 14% potassium. The typical average air temperature was 24° C.

Plant description:

*Habit.*—Vigorous.

*Life cycle.*—Tender perennial.

*Height.*—35.0 cm from soil line to top of foliage.

*Spread.*—60.0 cm.

*Time to produce a rooted cutting.*—About 4 weeks.

*Time to bloom from propagation.*—6 to 8 weeks.

*Flowering requirements.*—Will flower so long as temperature is above 5° C.

*Temperature tolerance.*—Plants have been observed as continuously flowering in a temperature range of 5° C. to 36° C.; plants can withstand high heat and humidity.

Branches:

*Number.*—3 main branches, 8 total branches.

*Length.*—Approximately 2.0 cm from soil line to first node; approximately 6.0 cm from first node to second node; approximately 30.0 cm total.

*Diameter* (*main branch*).—1.0 cm.

*Color.*—RHS 187A (Greyed-Purple).

Stems:

*Length.*—16.0 cm to 18.0 cm.

*Diameter.*—0.6 cm.

*Internode length.*—9.0 cm.

*Color.*—RHS 144A (Yellow-Green) and RHS 187A (Greyed-Purple).

*Stem description.*—Strong; circular cross-section, smooth and shiny.

*Pubescence.*—None.

*Anthocyanin color.*—RHS 187A (Greyed-Purple).

Leaves:

*Arrangement.*—Whorled with up to 5 leaves per node, opposite if only 2 leaves at 1 node.

*Length.*—14.0 cm.

*Width.*—4.5 cm.

*Shape.*—Lanceolate, curled.

*Margin.*—Ciliate; also slightly serrate.

*Apex.*—Acuminate.

*Base.*—Attenuate.

*Texture.*—Dull; waxy.

*Color.*—Upper surface: Closest to RHS 137A (Green). Lower surface: RHS 138A (Green).

*Fragrance.*—Absent.

*Pubescence.*—Glabrous.

*Variegation* (*both upper and lower surfaces*).—Absent.

*Venation.*—Pinnate.

*Venation color.*—Upper surface: RHS 138C (Green). Lower surface: RHS 138D (Green).

*Petioles.*—Length: 1.0 cm. Diameter: 0.4 cm. Color: RHS 138D (Green). Texture: Smooth, glabrous.

Flower buds:

*Shape.*—Deltoid, longitudinal cross-section.

*Length.*—2.0 cm.

*Diameter.*—1.0 cm.

*Color.*—RHS 59C (Red-Purple) and RHS 143C (Green).

*Texture.*—Glabrous.

Inflorescence:

*Blooming habit.*—Will flower as long as the temperature is above 5° C.

*Inflorescence type.*—Single flower with spur.

*Number of flowers per node.*—1 to 3 flowers in bloom; about 4 to 6 flower buds per node.

*Number of flowers per plant.*—Approximately 14 in bloom.

*Lastingness of individual blooms on the plant.*—14 days.

*Fragrance.*—Absent.

Peduncles:

*Length.*—4.5 cm.

*Diameter.*—0.2 cm.

*Color.*—RHS 73B (Red-Purple).

*Texture.*—Smooth, glabrous.

Corolla:

*Shape.*—Roughly circular with 5 radial petals.

*Diameter.*—Approximately 6.0 cm.

*Depth.*—1.0 cm.

Petals:

*Shape.*—Obcordate.

*Length.*—2.0 cm.

*Width.*—2.5 cm.

*Apex.*—Emarginate (cleaved).

*Base.*—Attenuate.

*Margin.*—Entire.

*Texture.*—Glabrous.

*Color.*—Upper surface: RHS 73A (Red-Purple). Lower surface: Closest to RHS 73B (Red-Purple). Eye zone: Closest to RHS 73A (Red-Purple).

Spur:

*Shape.*—Tubular, curved downward.

*Color.*—Closest to RHS 73B (Red-Purple).

*Length.*—4.5 cm.

*Diameter.*—0.2 cm.

Sepals:

*Shape.*—Lanceolate.

*Number.*—2.

*Color.*—RHS 139D (Green).
*Length.*—1.0 cm.
*Diameter.*—0.5 cm.
*Apex.*—Caudate.
*Base.*—Subcordate.
*Margin.*—Entire.
*Texture.*—Glabrous.

Reproductive organs:

*Stamens.*—Form: Fused; split into 4 lobes. Number: Many. Filament length: 0.5 cm. Filament color: RHS 73D (Red-Purple). Anther length: 0.4 cm. Anther color: RHS 155A (White). Pollen amount: Abundant. Pollen color: RHS 155D (White). Pollen description: Powdery.

*Pistil.*—Number: 5. Stigma color: RHS 143A (Green). Style color: RHS 143A (Green). Style length: 0.5 cm.

*Ovary arrangement.*—Parietal.

*Ovary surface color.*—RHS 143A (Green).

Fruit and seed set: No seed set observed.

Disease and insect resistance: No particular resistance or susceptibility has been observed.

COMPARISON WITH PARENTAL AND COMMERCIAL VARIETIES

'SAKIMP021' is similar to the female parent 'NG-02SM-1 3' and the male parent 'EL-1A-1'; however, there is a difference as listed in Table 1:

TABLE 1

Comparison of Characteristics between 'SAKIMP021' and Parental Varieties

| Characteristic | 'SAKIMP021' | Male Parent 'EL-1A-1' | Female Parent 'NG-02SM-1 3' |
|---|---|---|---|
| Flower color | Pink | Lilac | Orange |

'SAKIMP021' is similar to the commercial *Impatiens* variety 'SAKIMP006' (U.S. Plant Pat. No. 19,501); however, there are differences as listed in Table 2:

TABLE 2

Comparison of Characteristics between 'SAKIMP021' and 'SAKIMP006'

| Characteristic | 'SAKIMP021' | 'SAKIMP006' |
|---|---|---|
| Petal color, upper surface | RHS 73A (Red-Purple) | RHS N74B (Red-Purple) |
| Petal color, lower surface | Closest to RHS 73B (Red-Purple) | RHS N74C (Red-Purple) with RHS N74A vein between petal lobes |
| Petal color, eye zone | Closest to RHS 73A (Red-Purple) | RHS N74A (Red-Purple) |

We claim:

1. A new and distinct variety of New Guinea *Impatiens* plant as shown and described herein.

* * * * *